United States Patent
Dottori et al.

(10) Patent No.: US 9,150,936 B2
(45) Date of Patent: Oct. 6, 2015

(54) CONDITIONING OF BIOMASS FOR IMPROVED C5/C6 SUGAR RELEASE PRIOR TO FERMENTATION

(75) Inventors: Frank A. Dottori, Temiscaming (CA); Robert Ashley Cooper Benson, North Bay (CA); Regis-Olivier Benech, Chatham (CA)

(73) Assignee: GreenField Specialty Alcohols Inc., Toronto (CA)

( * ) Notice: Subject to any disclaimer, the term of this patent is extended or adjusted under 35 U.S.C. 154(b) by 749 days.

(21) Appl. No.: 13/547,508

(22) Filed: Jul. 12, 2012

(65) Prior Publication Data
US 2013/0014749 A1    Jan. 17, 2013

Related U.S. Application Data

(60) Provisional application No. 61/508,407, filed on Jul. 15, 2011.

(51) Int. Cl.
*C13K 13/00* (2006.01)
*C13K 1/02* (2006.01)

(52) U.S. Cl.
CPC .............. *C13K 1/02* (2013.01); *C12P 2201/00* (2013.01)

(58) Field of Classification Search
None
See application file for complete search history.

(56) References Cited

U.S. PATENT DOCUMENTS

| 2,681,871 A | 6/1954 | Wallace |
|---|---|---|
| 3,939,286 A | 2/1976 | Jelks |
| 4,136,207 A | 1/1979 | Bender |
| 4,461,648 A | 7/1984 | Foody |
| 5,424,417 A | 6/1995 | Torget et al. |
| 5,628,830 A | 5/1997 | Brink |
| 6,090,595 A | 7/2000 | Foody et al. |
| 6,419,788 B1 | 7/2002 | Wingerson |

(Continued)

FOREIGN PATENT DOCUMENTS

| CA | 2464090 A1 | 5/2003 |
|---|---|---|
| CA | 2638152 | 1/2010 |

(Continued)

OTHER PUBLICATIONS

Ewanick et al, The effect of biomass moisture content on bioethanol yields from steam pretreated switchgrass and sugarcane bagasse, Oct. 2010, Bioresource Technology 102, pp. 2651-2658.*

(Continued)

*Primary Examiner* — Melvin C Mayes
*Assistant Examiner* — Stefanie Cohen
(74) *Attorney, Agent, or Firm* — Borden Ladner Gervais LLP

(57) ABSTRACT

Disclosed is an improvement in a conventional process for C5 and C6 sugar recovery from lignocellulosic biomass for fermentation to ethanol, which process including the conventional steps of pretreatment of the biomass with steam at elevated temperature and pressure, collection of C5 sugars from hemicellulose breakdown, cellulose hydrolysis and collection of C6 sugars from cellulose breakdown. The improvement includes conditioning of the biomass prior to the pretreatment step by heating the biomass with steam for a time period between 5 minutes to 60 minutes to achieve a steam treated biomass having a temperature of about 80 to 100° C.; and adjusting a moisture content of the steam treated biomass to about 45% to 80%. An increased recovery of C5 and C6 sugars is achieved compared to the conventional process.

32 Claims, 1 Drawing Sheet

(56) References Cited

U.S. PATENT DOCUMENTS

| | | | |
|---|---|---|---|
| 6,878,212 | B1 | 4/2005 | Pinatti et al. |
| 7,815,741 | B2 | 10/2010 | Olson |
| 2008/0044877 | A1 | 2/2008 | Penttila et al. |
| 2008/0196847 | A1 | 8/2008 | Pieter Van Heiningen et al. |
| 2009/0023187 | A1 | 1/2009 | Foody et al. |
| 2009/0221814 | A1 | 9/2009 | Pschorn et al. |
| 2010/0065128 | A1 | 3/2010 | Benson et al. |
| 2010/0269990 | A1 | 10/2010 | Dottori et al. |

FOREIGN PATENT DOCUMENTS

| | | |
|---|---|---|
| CA | 2701194 A1 | 10/2010 |
| CA | 2715458 | 10/2010 |
| CN | 1352716 A | 6/2002 |
| CN | 101223288 A | 7/2008 |
| CN | 101691537 A | 4/2010 |
| WO | 02/14598 A1 | 2/2002 |
| WO | 2008/073186 A2 | 6/2008 |
| WO | 2008/095098 A2 | 8/2008 |
| WO | 2008/137639 A1 | 11/2008 |
| WO | 2010/009548 A1 | 1/2010 |
| WO | 2010/071805 A2 | 6/2010 |

OTHER PUBLICATIONS

Shapouri et al., "Estimating the net energy balance of corn ethanol; An Economic Research Service Report", USDA Report 721, Jul. 1995, 13 pages.
Shapouri et al., "The Energy Balance of corn ethanol: an update", USDA Report 814, Jul. 2002, 19 pages.
Chow et al., "Energy resources and global development", Science, vol. 302, Nov. 28, 2003, pp. 1528-1531.
Wald et al., "The Energy challenge: A Renewed push for ethanol, without the corn", New York Times, Apr. 17, 2007, 5 pages.
Greer, "Commercializing cellulosic ethanol", Biocycle, vol. 49, Nov. 2008, No. 11, 4 pages.
Hill et al. "Environmental, economic, and energetic costs and benefits of biodiesel and ethanol biofuels", Proc. Natl. Acad. Sci. USA, Jul. 25, 2006, vol. 103, No. 30, pp. 11206-11210.
Farrell et al., "Ethanol can contribute to energy and environmental goals", Science, Jan. 27, 2006, vol. 311, 23 pages.
Somerville, "Biofuels", Current biology, 2007, vol. 17, No. 4, pp. 115-119.
Schuetzle et al., "Alcohol fuels from biomass-Assessment of production technologies", Western Governors' Association National Biomass and Regional Partnership Report, Jul. 2007, pp. 1-119, 125 pages.
McMillan et al., "Pretreatment of lignocellulosic biomass", Biprocessing Branch, Alternative Fuels Division, National Renewable Energy Laboratory, 1994, American Chemical Society, pp. 292-324.
Fan et al., "The nature of lignocellulosics and their pretreatments for enzymatic hydrolysis", Advances in Biochemical Engineering, 1982, vol. 23, pp. 158-187.
Yang et al., "Pretreatment: the key to unlocking low-cost cellulosic ethanol", Biofuels, Bioproducts and Biorefinering, Jan. 2008, published online Dec. 17, 2007, vol. 2, pp. 26-40.
Chum et al., "Biomass and Renewable Fuels", Fuel Processing Technology, Jun. 2001, vol. 71, Elsevier Science B. V., United States of America, pp. 187-195.
Wyman, Handbook on Bioethanol: Production and Utilization, Jul. 1996, Taylor and Francis, United States of America, pp. 10-12.
Aoyama, "Steaming Treatment of Bamboo Grass. II. Characterization of Solubilised Hemicellulose and Enzymatic Digestibility of Water-Extracted Residue", Cellulose Chemistry and Technology, received for publication Jan. 18, 1996, 30, pp. 385-393.
Badal, "Hemicellulsoe Bioconversion", J. Ind. Microb.Biotechnol, vol. 30, No. 5, Available Online Apr. 16, 2003, pp. 279-291.
Canadian Patent Application No. 2,738,886, Office Action dated Aug. 3, 2011.
Carvalheiro et al., "Production of oligosaccharides byautohydrolysis of brewery's spent grain". Bioressource Technology, 91, Available Online Jul. 16, 2003, 2004, pp. 93-100.
Clarke, "Chemistry and structure of cellulose and heteroxylan", In Biodegradation of cellulose: Enzymology and Biotechnology, Lancaster, Pa: Technomic Press, 1996, pp. 1-21.
Ferrari et al., "Ethanol Production From Eucalyptus Wood Hemicellulose Hydrolyzate by *Pichia stipitis*", Biotechnology and Bioengineering, vol. 40, Available Online Feb. 19, 2004, 1992, pp. 753-759.
Gans et al., "Process Development for Plug Flow Acid Hydrolysis and Conversion of Lignocellulosics to Ethanol". In Bioenergy: Proc7th Can. Bioenergy R&D Semina, E. Hogan, ed., NRC Canada, 1989, pp. 419-423.
Garrote et al., "Kinetic modelling of corncob autohydrolysis", Process Biochemistry, vol. 36, Available Online Jan. 11, 2001,pp. 587-578, pp. 571-578.
Garrote et al., "Autohydrolysis of corncob: study of non-isothermal operation for xylooligosaccharide production", Journal of Food Engineering, vol. 52, Available Online Feb. 21, 2002, pp. 211-218.
Garrote et al., "Mild autohydrolysis : an environmentally friendly technology for xylooligosaccharide from wood", Journal of Chemical Technology and Biotechnology, vol. 74, 1999, accepted for publication Jul. 12, 1999, pp. 1101-1109.
Graves et al., "Effects of pH and lactic or acetic acid on ethanol productivity by *Saccharomyces cerevisiae* in corn mash", J. Ind Microbiol Biotechnol, vol. 33, Feb. 21, 2006, pp. 469-474.
International Patent Application No. PCT/CA2010/000051, International Search Report dated Mar. 16, 2010, 11 pages.
International Patent Application No. PCT/CA2012/050481, International Search Report dated Oct. 11, 2012, 7 pages.
Krisch et al., "Ethanol and acetic acid tolerance in free and immobilized cells of *Saccharomyces cerevisiae* and *Acetobacter aceti*", Biotechnolgy Letters, vol. 19, No. 6, Jun. 1997, pp. 525-528.
Kuyper et al., "Minimal metabolic engineering of *Saccharomyces cerevisiae* for efficient anaerobic xylose fermentation: a proof of principle", FEMS Yeast Research, vol. 4, Feb. 20, 2004, pp. 655-664.
Lawford et al., "Effect of pH and Acetic Acid on Glucose and Xylose Metabolism by a Genetically Engineered Ethanologenic *Escherichia coli*", Applied Biochemistry and Biotechnology, vol. 39/40, 1993, pp. 301-322.
Lawford et al., "Effect of Acetic Acid on Xylose Conversion to Ethanol by Genetically Engineered *E. coli*", Applied Biochemistry and Biotechnology, The Human Press Inc., vol. 34/35, 1992, pp. 485-204.
McMillan, "Hemicellulose conversion to Ethanol", Handbook on Bioethanol: Production and Utilization, C. Wyman, Editor, Taylor and Francis, Washington DC, Jul. 1, 1996, pp. 287-313.
McMillan, "Conversion of Hemicellulose Hydrolyzates to Ethanol", Enzymatic Conversion of Biomass for Fuels Production. M.E. Himmel, J.O. Baker and R.P. Overend, eds., 1994, ACS Symposium Series 566, American Chemical Society, pp. 411-437.
Moura et al., "In vitro fermentation of xylo-oligosaccharides from corn cobs autohydrolysis by *Bifidobacterium* and *Lactobacillus* strains", Swiss Society of Food and Science Technology, Available Online Oct. 2, 2006, LWT 40, pp. 963-972.
Narendranath et al., "Acetic Acid and Lactic Acid Inhibition of Growth of *Saccharomyces cerevisiae* by Different Mechanisms", J. American Society of Brewing Chemists, vol. 59, No. 4, 2001, pp. 187-194.
Narendranath et al., "Effects of acetic acid and lactic acid on the growth of *Saccharomyces cerevisiae* in a minimal medium", Journal of Industrial Microbiology & Biotechnology, 26/3, 2001, accepted for publication Sep. 2000, pp. 171-177.
Pampulha et al., "Activity of glycolytic enzymes of *Saccharomyces cerevisiae* in the presence of acetic acid", Appl. Microbiol. Biotechnol, vol. 34, Available Online Aug. 10, 1990, pp. 375-380.
European Patent Application No. 12814550.5-1357, Extended European Search Report dated Feb. 9, 2015, 6 pages.
Ruzene et al., Hydrothermal treatments of corn cobs and hemicellulose extraction, Proceedings of the 10th International Chemical and Biological Engineering Conference—CHEMPOR2008. E.C. Ferreira and M. Mota (Eds.) Braga, Portugal, Sep. 4-6, 2008.

(56) References Cited

OTHER PUBLICATIONS

Rydholdm, "Pulping Processes", Wood Chemistry, Interscience Publisher, N.Y., 1965, corrected printing Sep. 1967, pp. 95-96.

Thomas et al., "Influence of Medium Buffering Capacity on Inhibition of *Saccharomyces cerevisiae* Growth by Acetic and Lactic Acids", Applied and Environmental Microbiology, Apr. 2002, pp. 1616-1623.

Torget et al., "Dilute-Acid Pretreatment of Corn Residues and Short-Rotation Woody Crops", Applied Biochemistry and Biotechnology, vol. 28/29, The Human Press Inc., 1991, pp. 75-86.

Torget et al., "Dilute-Acid Pretreatment of Two Short-Rotation Herbaceous Crops", Applied Biochemistry and Biotechnology, vol. 34/35, The Human Press Inc., 1992, pp. 115-123.

Vasquez et al., "Enhancing the potential of oligosaccharides from corncob autohydrolysis as prebiotic food ingredients", Industrial Crops and Products, vol. 24, Available Online Jun. 2, 2006, pp. 152-159.

Walther et al., "The influence of aeration and hemicellulose sugars on xylitol production by *Candida tropicalis*", Bioresource Technology, vol. 76, Available Online Oct. 2000, pp. 213-220.

PCT Patent Application No. CA2012/050481, Search Report dated Oct. 11, 2012.

\* cited by examiner

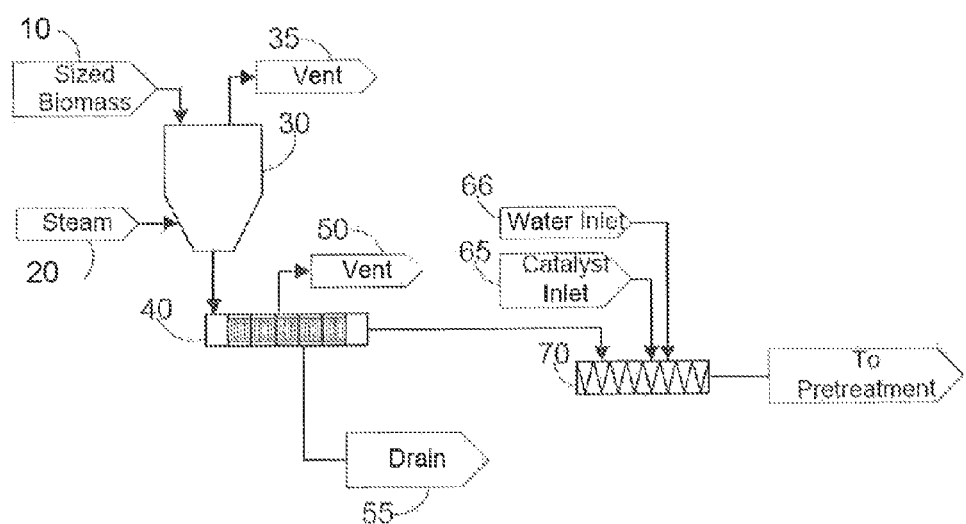

CONDITIONING OF BIOMASS FOR IMPROVED C5/C6 SUGAR RELEASE PRIOR TO FERMENTATION

This application claims the benefit of priority of U.S. Provisional Patent Application No. 61/508,407 filed Jul. 15, 2011, the contents of which is incorporated herein by reference.

FIELD OF THE INVENTION

The invention relates to the conditioning of lignocellulosic biomass as part of a biochemical ethanol production process, in particular to conditioning prior to pretreatment for hemicellulose breakdown and removal.

BACKGROUND AND DESCRIPTION OF PRIOR ART

There is a growing demand for transportation fuels made from renewable feedstocks. These renewable fuels displace fossil fuels resulting in a reduction of greenhouse gas emissions, along with other benefits (1-3). Biofuels include fuel ethanol. Fuel ethanol is roduced from biomass by converting starch or cellulose to sugars, fermenting the sugars to ethanol, and then distilling and dehydrating the ethanol to create a high-octane fuel that can substitute in whole or in part for gasoline.

In North America, the feedstock for the production of fuel ethanol is primarily corn, while in Brazil sugar cane is used. There are disadvantages to using potential food or feed plants to produce fuel. Moreover, the availability of such feedstocks is limited by the overall available area of suitable agricultural land. Therefore, efforts are being made to generate ethanol from non-food sources, such as cellulose, and from crops that do not require prime agricultural land, for example miscanthus. Cellulose is one of the most abundant organic materials on earth. It is present in many forms of biomass, including agricultural residues like corn stover and corncobs, woody residues and other plant materials. Cellulose is a polymer of glucose, as is starch. However, the isolation of reactive cellulose from lignocellulosic biomass and hydrolysis to C6 sugar monomers has its challenges. One non-food source of C6 sugars is lignocellulosic biomass.

Lignocellulosic biomass may be classified into four main categories: (1) wood residues (sawdust, bark or other), (2) municipal paper waste, (3) agricultural residues (including corn stover, corncobs and sugarcane bagasse), and (4) dedicated energy crops (which are mostly composed of fast growing tall, woody grasses such as switchgrass and miscanthus).

Lignocellulosic biomass is composed of three primary polymers that make up plant cell walls: Cellulose, hemicellulose, and lignin. Cellulose fibres, which contain only anhydrous glucose (C6 sugar), are locked into a rigid structure of hemicellulose and lignin. Lignin and hemicelluloses form chemically linked complexes that bind water soluble hemicelluloses into a three dimensional array, cemented together by lignin. Lignin covers the cellulose microfibrils and protects them from enzymatic and chemical degradation. These polymers provide plant cell walls with strength and resistance to degradation, which makes lignocellulosic biomass a challenge to use as substrate for biofuel production.

Hemicelluloses are polysaccharides and include xylan, glucuronoxylan, arabinoxylan, glucomannan, and xyloglucan, which all contain many different C5 or C6 sugar monomers. For instance, besides glucose, sugar monomers in hemicellulose can include xylose, mannose, galactose, rhamnose, and arabinose. Hemicelluloses contain most of the D-pentose sugars, and occasionally small amounts of L-sugars as well. Xylose is always the sugar monomer present in the largest amount, which is why hemicellulose content is often expressed in terms of xylose equivalent content, as will be discussed further below. Xylose is a monosaccharide of the aldopentose type, which means it contains five carbon atoms (C5 sugar) and includes an aldehyde functional group. Cellulose is crystalline, strong and resistant to hydrolysis, while hemicellulose has a random, amorphous structure with little strength and is easily hydrolyzed by dilute acid or base, or by hemicellulase enzymes.

There are two main approaches to the production of fuel ethanol from biomass: thermochemical and biochemical. Thermochemical processes convert the biomass to a reactive gas called syngas. Syngas is converted at high temperature and pressure to ethanol by a series of catalyzed processes. Biochemical processes use biocatalysts called enzymes to convert the cellulose content to sugars (C5 and C6), which are then fermented to ethanol and other fuels such as butanol. The biochemical processes generally exploit the different susceptibility to hydrolysis of hemicellulose and cellulose, by hydrolyzing the hemicellulose and cellulose in different steps.

Biochemical conversion of lignocellulosic biomass to ethanol in general involves five basic steps (1) Preparation—the target biomass is cleaned and adjusted for size and moisture content; (2) Pretreatment—exposure of the raw biomass to elevated pressure and temperature for a specified duration; with or without catalyzing additives to hydrolyze the hemicellulose separately from the cellulose; (3) Cellulose hydrolysis—conversion of the cellulose in the pretreated biomass to simple C6 sugars using special enzyme preparations to hydrolyze the pretreated plant cell-wall polysaccharides; (4) Fermentation, mediated by bacteria or yeast, to convert these sugars to fuel such as ethanol; and (5) Distillation and Dehydration of the ethanol/fuel.

Certain pretreatment methods employ chemical additives, such as acids, to catalyze the hydrolysis of hemicellulose and/or alkalis to remove lignin. These additives as well as many of the breakdown products they generate during the pretreatment process, such as lignin and some soluble lignin derivatives, are either toxic to yeast, or inhibit hydrolysis, or both. Furthermore, all forms of lignocellulosic biomass have some level of sterols, fatty acids, ethers and other extractives that can also be inhibitory.

One approach to address the inhibitory effect of these substances is the use of harsher pre-treatment conditions, which can for example be tailored to effectively hydrolyze and degrade the hemicellulose to such an extent that very little xylose and xylo-oligosaccharides remain to interfere with the cellulose enzymes. However this approach creates another significant disadvantage in that it causes significant cellulose degradation, which then reduces glucose yield and ultimately the ethanol yield, often creating a commercially significant reduction of the overall ethanol process efficiency, even in the virtual absence of inhibitory compounds.

In another approach xylanases are used to completely hydrolyze the xylan oligomers to xylose and lessen the inhibitory effect of these oligomers. However, although this approach is somewhat effective, it produces high levels of xylose which is itself an inhibitor. Moreover, the other inhibitory compounds generated in the pretreatment step from decomposition of the hemicellulose are still present. Thus, although the overall yield is better, in the end this approach is not commercially viable due to the added cost for the xylanases and the cost of still required elevated cellulase levels due to the other inhibitory substances.

All pretreatment processes, generally result in significant breakdown of the biomass, in particular the hemicellulose component, which leads to the generation of various C5 sugars and other hemicellulose breakdown products. Hemicellulose decomposition products such as formic acid, furfural and hydroxyl methyl furfural etc. are produced during pretreatment which carry through to and inhibit the hydrolysis and fermentation processes. Thus, these hemicellulose decomposition products reduce the effectiveness of the cellulose hydrolyzing enzymes, thereby requiring the use of increased levels of added enzyme, the cost of which is an important factor in providing a cost effective commercial process.

The breakdown products inhibitory to the downstream cellulose and/or sugar fermentation processes are usually separated from the biomass prior to cellulose hydrolysis, to minimize any potentially inhibitory effects on ethanol yield. However, although the overall ethanol yield could be significantly improved if the C5 sugars originating from the hemicellulose could also be used in the sugar fermentation step, separating the C5 sugars from the removed inhibitory hydrocellulose breakdown product stream is cost intensive and uneconomical. Thus, an efficient and economical process is desired which increases the yield of C5 and C6 sugars in a conventional lignocellulosic biofuel production process.

SUMMARY OF THE INVENTION

It is now an object to provide an improved biofuel production process using lignocellulosic biomass.

In particular, the invention provides an improvement in a process for C5/C6 sugar recovery from lignocellulosic biomass for fermentation to ethanol, including the steps of pretreatment of the biomass with steam at elevated temperature and pressure, collection of C5 sugars from hemicellulose breakdown, cellulose hydrolysis and collection of C6 sugars from cellulose breakdown. The improvement resides in the additional step of conditioning of the biomass prior to the pretreatment step by. The conditioning includes the steps of heating the biomass with steam for a time period between 5 minutes to 60 minutes, preferably 10 to 60 minutes, more preferably 10 to 30 minutes, even more preferably 15 to 30 minutes, most preferably about 20 minutes, to achieve a steam treated biomass having a temperature of between 80° C. to 100° C.; and adjusting a moisture content of the steam treated biomass to between 45% to 80%, preferably 55% to 80%, more preferably 65% to 80%, even more preferably 70% to 75%.

In one embodiment, the invention provides a process, wherein the heating with steam is conducted for 27-55 minutes to achieve a biomass temperature of 90° C., preferably 20-40 minutes to achieve a biomass temperature of 95° C., more preferably 15-30 minutes to achieve a biomass temperature of 99° C., even more preferably 14-28 minutes to achieve a biomass temperature of 100° C.

In another embodiment, the pre-conditioned biomass contains 68-72% moisture content and 0.07% to 0.09% sulfuric acid content by weight prior to the pretreatment process, preferably 68-72% moisture content and 0.07% to 0.09% sulfuric acid content.

The inventors surprisingly discovered that the results of conventional pretreatment such as yield, recovery, reactivity and process time for the conversion of cellulose and hemicellulose to ethanol and/or other valuable chemicals can be improved by adding the conditioning step. Conditioning the biomass prior to pretreatment was found to improve cellulose reactivity (which reduces cellulose hydrolysis time); to minimize the use of enzymes to convert cellulose to glucose; to maximize the removal of impurities and toxic compounds; to increase the recovery of the hemicellulose fraction; to optimize the fermentation process; to reduce fermentation time; and to increase overall yield.

The inventors have discovered that one or more of these results above can be improved by the conditioning process that controls the moisture of the biomass prior to pretreatment; and/or the temperature and retention time of the steam heating step. In addition, the inventors have further discovered that an additional improvement can be achieved by subjecting the biomass, as part of the conditioning step, to a squeezing or compression step to extract toxic impurities and improve catalyst and water impregnation after the steam heating step.

This conditioning process improves the results of pretreatment processes. The conditioning also brings the biomass to a standard set of conditions prior to pretreatment which is important for consistently optimum pretreatment results. Such conditioning can also soften the fibers and provide even distribution of moisture and chemical catalyst. Without being bound by this theory, the inventors theorize that the conditioning enables a selective removal of the soluble inhibitory components in the lignocellulosic biomass, without the removal of significant amounts of the C5 sugar monomer components of the hemicellulose, thus resulting in a lowered content of inhibitory compounds and an increased level of C5 sugars in the biomass prior to pretreatment allowing for the recovery of a hemicellulose breakdown stream after pretreatment which includes fewer, or lower amounts of inhibitory compounds in addition to C5 sugars.

BRIEF DESCRIPTION OF THE DRAWING

FIG. 1 shows a biofuel production process including a conditioning process in accordance with this application.

DETAILED DESCRIPTION OF PREFERRED EMBODIMENTS

Before explaining the present invention in detail, it is to be understood that the invention is not limited to the preferred embodiments contained herein.

The invention is capable of other embodiments and of being practiced or carried out in a variety of ways. It is to be understood that the phraseology and terminology employed herein are for the purpose of description and not of limitation.

As shown in FIG. 1, sized biomass 10 is conveyed into a steaming bin or container 30. Biomass is typically received for processing in a semi-dry state having a moisture content of less than 50%, and as low as 10%. For example corncobs usually are obtained after the corn has dried in the field to a moisture content of 15-35%. Upon arrival at the processing plant, the biomass, such as corncobs, is chopped to a convenient size. The biomass is typically chopped to a length of about 1 inch. Water can be added to the sized biomass to raise the moisture content prior to steam heating step in the conditioning process of the invention.

Steam 20 is injected proximate to a bottom of the container at one or more spots to heat the sized biomass 10. Air, steam, and non-condensable gases are vented from a vent 35 proximate to a top of the container 30. As the steam 20 drives heat up the container 30, the sized biomass 10 absorbs moisture and becomes evenly charged with moisture. During the steaming, the temperature rises and non-condensable gases are driven off. In one embodiment, the sized biomass 10 is heated to 80 to 100 Degrees Celsius with steam at atmospheric pressure for a period of 10 to 60 minutes.

Steam heated biomass 15 is drawn from the bottom of the container 30 and is fed to any type of lignocellulosic biomass pretreatment process. In one embodiment, the steam heated biomass is first fed to a compression or squeezing device 40 such as a screw press, modular screw device (MSD), etc. It is contemplated that any device that squeezes or compresses biomass could be used to compress the biomass and to drain extracted fluids. In one embodiment, the squeezing device 40 squeezes the steam heated biomass 15 with a 2-1 to 6-1 compression ratio, preferably a 3-1 to 4-1 compression ratio, most preferably a 4-1 ratio. The squeezing device 40 has a vent 50 to vent gases if necessary, and a drain 55 to drain the extracted fluids which include inhibitory extracts squeezed from the steam heated biomass 15. During the squeezing process, a portion of the liquid is removed from the steam heated biomass 15 along with compounds that adversely affect downstream processing steps in the manufacture of ethanol such as resins, tall oils and fatty acids.

Squeezed biomass 45 is then fed to a mixing device 70. The mixing device 70 mixes the squeezed biomass 45 with the optional proportion of water through a water inlet 66 and/or optional amount of catalyst through a catalyst inlet 65. In one embodiment, the catalyst is acid and may range in concentration from between 0 and 5% by volume and the biomass water content ranges from 60% to 80%. In one embodiment, this mixing step can be incorporated right at the discharge of the squeezing device 40. A suitable mixing device 70 in one instance could be as simple as one or more injection or addition points along the outlet of the squeezing device 40. This is operable because the squeezed biomass 45 is similar to a squeezed sponge and it can readily and actively absorb the water and chemicals.

In a preferred embodiment of the mixing step, water and/or water and catalyst such as sulfuric acid are added to bring the moisture content to greater than 65%. The inventors have found that the particular combination of steps in the conditioning of the biomass prior to pretreatment has a significant commercially positive effect by reducing the digestion time of the corncobs by up to greater than 60% and by increasing hemicellulose recovery in a soluble form by over 40%, as illustrated in Example 1 below.

In the Examples, pre-conditioned corncobs were pre-treated with steam at a severity index value of 4.0 (205° C. for 8 minutes), as described in pending U.S. patent application Ser. No. 12/560,843, now U.S. Pat. No. 8,287,651, the contents of which are hereby incorporated by reference, followed by enzymatic hydrolysis at 15 to 20% consistency.

If the particular biomass contains significant resins, oils, fatty acids, tall oils etc., such as those contained in woodchips, removal or at least partial removal of these resins, oils, fatty acids, tall oils, etc. during the squeezing step of the conditioning process improves the downstream enzyme hydrolysis and fermentation performance.

In addition, it was found that for biomass that required the addition of chemical catalyst, the squeezing step prior to catalyst addition aided in the absorption of the catalyst more evenly throughout the biomass improving the recovery and solubililization of the hemicellulose.

The mixing device 70 discharges into a pre-treatment system.

Example 1

Adjusting Moisture Content Improves Cellulose Digestibility and Hemicellulose Recovery

TABLE 1

Effect of moisture content in incoming corn cobs on recovery of hemicellulose
Table 1. Effect of moisture content in incoming corn cobs on recovery of hemicellulose

| | Moisture (%) | | | | | | |
|---|---|---|---|---|---|---|---|
| Incoming cobs | 69 | 66 | 54 | 46 | 35 | 29 | 11 |
| Hemicellulose Recovery (% of incoming) | 72 | 71 | 62 | 59 | 50 | 45 | 27 |
| Soluble hemicellulose sugars (kg/mtdm incoming corn cobs) | 253 | 249 | 218 | 207 | 176 | 158 | 95 |
| Hemicellulose sugar monomers (kg/mtdm incoming corn cobs) | 211 | 208 | 182 | 173 | 147 | 132 | 79 |

Table 1 illustrates that hemicellulose sugar recovery increased by greater than 40% as moisture content was increased from 35% to 66%. In order to further increase the ratio of sugar monomers over oligomers, the recovered soluble hemicellulose sugars can be hydrolyzed post recovery either with hemicellulase enzymes or acid catalyst.

TABLE 2

Effect of moisture content in incoming corn cobs on cellulose digestibility
Table 2. Effect of moisture content in incoming corn cobs on cellulose digestibility and resulting production of glucose monomers

| | Moisture (%) | | | | | | |
|---|---|---|---|---|---|---|---|
| Incoming cobs | 69 | 66 | 54 | 46 | 35 | 29 | 11 |
| Glucose monomers (kg/mtdm incoming corn cobs) | 342 | 343 | 339 | 341 | 322 | 307 | 280 |

Hydrolysis conditions: 110 hours, 17% consistency fed batch hydrolysis with 0.215% (w/w DM) enzyme on cobs Digestibility is expressed as t90%, meaning that 90% of the available cellulose is converted in the time shown. The cellulose digestibility of pre-hydrolysates produced from cobs with varying moisture contents improved by about 70% as the moisture increased from 35% to 66%. Table 2 illustrates that when going from incoming moisture of 11% to 66% the digestion time decreases by greater than 60%.

Example 2

Pre-Heating with Steam Improves Cellulose Digestibility

Corncobs at 50% moisture were pre-heated with steam at atmospheric pressure with low pressure (5 psig) steam for 10 minutes prior to pre-treatment as described in pending U.S. patent application Ser. No. 12/560,843, now U.S. Pat. No. 8,287,651. The results of cellulose digestibility were compared (Table 1) to a control using 1 minute of pre-steaming at 300 psi using super heated steam.

TABLE 3

Effect of steaming on cellulose digestibility
Table 3. Effect of steaming on cellulose digestibility
and resulting production of glucose monomers

| | | Steam heating prior to pretreatment(1) & Pre-treatment conditions (2) | |
|---|---|---|---|
| Glucose monomers (kg/mtdm incoming cobs) | | (1) 1 min, 300 psig (2) 235 psig, 8 min | 10 min, atmospheric pressure |
| Enzyme load (% w/w, DM on cobs) | 0.225 | 342 | 360 |
| | 0.295 | 368 | 375 |

Table 3. Effect of steaming on cellulose digestibility

The longer steam heating time reduced the hydrolysis time by 18% to 24% depending on the enzyme dosage. Hemicellulose sugar recovery was not affected by the additional steam heating.

The combined effect of controlling moisture and steam heating times during the conditioning of corncobs as seen in Tables 2 and 3 respectively has a significant cumulative effect on the enzyme hydrolysis time and sugar (C5 and C6) recovery. Controlling the steam heating and moisture and combining those steps with a squeezing step as outlined above, provides maximum flexibility in treatment options, which will allow those skilled in the art to optimize known pretreatment processes.

What is claimed is:

1. In a process for C5 and C6 sugar recovery from lignocellulosic biomass for fermentation to ethanol, including the steps of pretreatment of the biomass with steam at elevated temperature and pressure, collection of C5 sugars from hemicellulose breakdown, cellulose hydrolysis and collection of C6 sugars from cellulose breakdown,
the improvement comprising
conditioning of the biomass prior to the pretreatment step by:
heating the biomass with steam for a time period between 5 minutes to 60 minutes to achieve a steam treated biomass having a temperature of about 80 to 100° C.; and
adjusting a moisture content of the steam treated biomass to about 45% to 80% by weight.

2. The process of claim 1, further including the step of adding to the conditioned biomass a user selected catalyst desired for the pretreatment process.

3. The process of claim 1, wherein, after the step of heating the biomass, the process comprises the additional step of squeezing the steam heated biomass for removing a liquid stream containing resins, oils, fatty acids or other inhibitors of downstream hydrolysis or fermentation.

4. The process of claim 3, further comprising the step of adding water, or water and a catalyst after the step of squeezing the steam heated biomass.

5. The process of claim 1, wherein the moisture content is adjusted to about 55% to 80% by weight.

6. The process of claim 1, wherein the moisture content is adjusted to about 65% to 80% by weight.

7. The process of claim 1, wherein the moisture content is adjusted to about 70% to 75% by weight.

8. The process of claim 1, wherein the heating step is carried out at atmospheric pressure.

9. The process of claim 8, wherein the time period is about 10 to 60 minutes.

10. The process of claim 8, wherein the time period is about 10 to 30 minutes.

11. The process of claim 8, wherein the time period is about 15 to 30 minutes.

12. The process of claim 8, wherein the time period is approximately 20 minutes.

13. The process of claim 8, wherein the temperature of the steam heated biomass is between 95° C. and 99° C.

14. The process of claim 3, wherein the steam heated biomass is squeezed at a 2-1 to 6-1 compression ratio.

15. The process of claim 14, wherein the steam heated biomass is squeezed at a 3-1 to 4-1 compression ratio.

16. The process of claim 15, wherein the steam heated biomass is squeezed at a 4-1 compression ratio.

17. The process of claim 1, further comprising the step of mixing the steam heated biomass with water, or water and a chemical catalyst prior to the pretreatment step to achieve a catalyst content of 0.07% to 0.09% of biomass by weight and 65% to 75% by weight moisture content.

18. The process of claim 17, wherein the chemical catalyst is sulfuric acid in a sulfuric acid concentration from 0.2% to 2% by volume.

19. The process of claim 18, where the sulfuric acid concentration is from 0.5% to 2% by volume.

20. The process of claim 19, where the sulfuric acid concentration is from 0.8% to 1.0% by volume.

21. The process of claim 1, wherein the biomass has a moisture content of 30-55% prior to the steam heating step of the conditioning.

22. The process of claim 1, wherein the heating with steam is conducted for 55 to 60 minutes for achieving a biomass temperature of about 80° C.

23. The process of claim 1, wherein the heating with steam is conducted for 40 to 60 minutes for achieving a biomass temperature of about 85° C.

24. The process of claim 1, wherein the heating with steam is conducted at a biomass temperature of 90° C. for 27 to 55 minutes.

25. The process of claim 1, wherein the heating with steam is conducted for 20 to 40 minutes for achieving a biomass temperature of about 95° C.

26. The process of claim 1, wherein the heating with steam is conducted for 15 to 30 minutes for achieving a biomass temperature of about 99° C.

27. The process of claim 1, wherein the heating with steam is conducted for 14 to 28 minutes for achieving a biomass temperature of about 100° C.

28. The process of claim 1, wherein the conditioned biomass contains 68-72% moisture content by weight prior to the pretreatment process.

29. The process of claim 28, wherein the biomass is corn cobs.

30. The process of claim 2, wherein the conditioned biomass contains 68-72% moisture content and 0.07% to 0.09% sulfuric acid content by weight prior to the pretreatment process.

31. The process of claim 2, wherein the conditioned biomass is corn cobs and contains 68-72% moisture content and 0.07% to 0.09% sulfuric acid content biomass by weight prior to the pretreatment process.

32. The process of claim 1, wherein volatile gasses are released during the conditioning process.

* * * * *